United States Patent
Oester et al.

(10) Patent No.: US 6,451,773 B1
(45) Date of Patent: Sep. 17, 2002

(54) CHITOSAN FORMULATION WITH AZELAIC ACID AND OTHER ACTIVES FOR THE TREATMENT OF ACNE

(75) Inventors: Dean A. Oester, Cincinnati, OH (US); Rolf Wachter, Duesseldorf (DE); Jeffrey A. Gates, West Chester, OH (US)

(73) Assignee: Cognis Corporation, Cincinnati, OH (US)

( * ) Notice: Subject to any disclaimer, the term of this patent is extended or adjusted under 35 U.S.C. 154(b) by 0 days.

(21) Appl. No.: 09/539,603

(22) Filed: Mar. 31, 2000

(51) Int. Cl.⁷ .............. A01N 43/04; A61K 7/00
(52) U.S. Cl. ............ 514/55; 514/859; 514/165; 428/401
(58) Field of Search ............ 514/55, 165, 859; 424/401

(56) References Cited

U.S. PATENT DOCUMENTS

| | | |
|---|---|---|
| 4,946,870 A | 8/1990 | Partain et al. |
| 5,019,567 A | 5/1991 | Philippe et al. |
| 5,023,090 A | 6/1991 | Levin |
| 5,260,292 A | 11/1993 | Robinson et al. |
| 5,505,949 A | 4/1996 | Benitez |
| 5,665,364 A * | 9/1997 | McAtee ............ 424/401 |
| 5,962,663 A * | 10/1999 | Wachter et al. ........ 536/20 |

OTHER PUBLICATIONS

Chemical Abstracts 118:87664, "Antiacne preparations containing chitin, chitosan, or the partial degradation products" (1992).*

* cited by examiner

*Primary Examiner*—Frederick Krass
(74) *Attorney, Agent, or Firm*—John E. Drach; Steven J. Trzaska

(57) ABSTRACT

A composition for treating acneiform eruption containing: (a) a chitosan having a molecular weight ranging from about 500,000 to about 5,000,000 g/mole and a degree of deacylation greater than 80%; (b) an acid-form active ingredient for treating acne; and (c) water.

11 Claims, No Drawings

CHITOSAN FORMULATION WITH AZELAIC ACID AND OTHER ACTIVES FOR THE TREATMENT OF ACNE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Acne is a common disease which afflicts the majority of all teenagers, along with a significant number of men and women of adult age. Acne vulgaris occurs most often on oily areas of the skin having high sebaceous gland concentration. These areas include the face, ears, behind the ears, chest, back and occasionally the neck and upper arms.

Acneiform eruptions can occur wherever there is a pilosebaceous unit or sebaceous follicle which does include the entire human skin surface. The basic lesion in acne is the comedo commonly known as the blackhead. The comedo is created by retention of layers of dead skin known as keratin in the lining of the follicles. In addition to hyperkeratosis, which is a thickening or retentative layering of keratin, there is also an accumulation of sebum which is the lipid-laden product of the sebaceous gland. The combination of keratin and sebum causes the follicular canal to become plugged, resulting in the formation of papules due to inflammation around the comedones. Depending on the degree of inflammation, pustules, cysts, nodules, granulomatous reactions, scars and keloids may develop.

Numerous treatments, both topical and systemic, are currently employed for the treatment of acne. Topical and systemic acne treatment compositions typically employ an active ingredient in combination with a carrier component. The active ingredients typically comprise an antibiotic/antibacterial such as tetracycline, erythromycin, clindamycin, and the like. With respect to topical treatment compositions, benzoyl peroxide is often used in combination with the antibiotic and carrier in order to potentiate the effectiveness of the antibiotic.

A disadvantage associated with the use of antibiotics is that upon prolonged usage, the bacteria targeted for elimination become resistant to antibiotic treatment.

Another causative factor for acne is the presence of bacteria in the follicular canal. Within the follicular canal are bacteria which are indigenous to the follicular lining. Among the bacteria flora present are anaerobic, gram positive organisms called Proprionibacterium acnes. It is believed that Propionibacterium acnes live in symbiosis on the keratin lined follicular canal. Propionibacterium acnes ingest sebum produced from the sebocytes of the sebaceous glands. This nascent sebum is largely lipid in composition and also contains DNA, RNA, proteins, and other cellular components that result from the breakdown of sebocytes themselves. The Propionibacterium acnes which are highly lipophilic, feed on the nascent sebum, found in sebaceous rich areas. If the nutrients increase due to an active and large sebaceous system, then colonization and high growth rates of Proprionibacterium acnes will occur. It has been shown that the resident bacterial flora will produce biologically active molecules such as histamine, extracellular enzymes, and peptides which may be responsible for the chemotaxis of the inflammatory infiltrate in acne vulgaris. Since the follicular lining in the pilosebaceous unit is intact, it has been theorized that if colonization of Proprionibacterium acnes occurs in sufficient numbers, they could produce antigenic molecules that promote the initiation of inflammation. Proprionibacterium acnes can produce proteases, lipase, and hyaluronate lyase all of which may serve as the catalysts or initiators of the inflammatory infiltrate which has been shown to be composed of neutrophils and lymphocytes.

Some of the more commonly used active compounds found in topical acne treatment formulations include topical erythromycin, clindamycin, benzoyl peroxide, sulfur, resorcinol, tetracycline derivatives, salicylic acid and the like.

A disadvantage associated with the use of such active compounds is that they cause epidermal irritation when applied onto the skin. The greater the amount of such active used, the higher the incidence of skin irritation.

BRIEF SUMMARY OF THE INVENTION

The present invention is directed to a composition for treating acneiform eruptions containing:

(a) an active ingredient used in treating acne vulgaris;

(b) a chitosan component having a molecular weight ranging from about 500,000 to about 5,000,000 g/mole, and a degree of deacylation greater than 80%; and (c) water.

The present invention is also directed to a process for treating acneiform eruptions present on human skin involving contacting human skin with the above-identified composition.

BRIEF DESCRIPTION OF THE SEVERAL VIEWS OF THE DRAWING

Not Applicable.

DETAILED DESCRIPTION OF THE INVENTION

Other than in the operating examples, or where otherwise indicated, all numbers expressing quantities of ingredients and reaction conditions are understood as being modified in all instances by the term "about".

The active compounds which may be employed in the present invention are the acid-based actives, well known in the art of acne treatment. Examples of suitable acid-based actives which may be used include, but are not limited to, azelaic acid, benzoyl peroxide, retinoic acid, and salicylic acid.

These acid-based active compounds require a carrier component to be used since they cannot, by themselves, be deposited directly onto human skin due to their harshness. The carrier component employed by the present invention is a high molecular weight chitosan having a high degree of deacylation.

Chitosans are biopolymers which belong to the group of hydrocolloids. In contrast to most hydrocolloids, which are negatively charged at biological pH values, chitosans are cationic biopolymers under these conditions. The positively charged chitosans are capable of interacting with oppositely charged surfaces and, accordingly, are used in cosmetic hair-care and body-care formulations and pharmaceutical formulations.

Chitosans are produced from chitin, preferably from the shell remains of crustaceans which are available in large quantities as inexpensive raw materials. Normally, the chitin is first deproteinized by addition of bases, demineralized by addition of mineral acids and, finally, deacylated by addition of strong bases.

One process for the production of a chitin degradation product involves treating crab shells with hydrochloric acid at room temperature, then deacylating with caustic soda solution over a period of 42 hours at 100° C., subsequently treating with more hydrochloric acid at room temperature and, finally, briefly aftertreating with sodium hydroxide solution, again at room temperature. According to this process, the deacetylation takes place in the second step. By contrast, the final treatment with sodium hydroxide solution is merely carried out to "fine tune" the degree of deacetylation and, accordingly, takes place at room temperature. Although this leads to low-ash products with a high degree of deacetylation and good solubility in organic acids, the molecular weight is very low and the film-forming properties are unsatisfactory.

In general, known chitosans are divided into two groups: the first group of products includes those which have a high degree of deacetylation, are soluble in organic acids and form low-viscosity solutions, but do not have satisfactory film-forming properties. The second group includes products which have a low degree of deacetylation, a relatively high molecular weight and good film-forming properties, but are poorly soluble in organic acids.

The chitosans employed in the present invention are distinguished from typical chitosans by virtue of their high molecular weight, as well as, a high degree of deacetylation. Thus, these chitosans possess good film-forming properties and are easily soluble in organic acids, such as those used as active compounds in the treatment of acne.

The chitosans of the present invention may be obtained by a process involving: (a) treating fresh crustacean shells with dilute aqueous mineral acid, (b) treating the resulting demineralized first intermediate product with aqueous alkali metal hydroxide solution, (c) treating the resulting lightly deproteinized second intermediate product with more dilute aqueous mineral acid, (d) optionally, drying the resulting decalcified third intermediate product to a residual water content of 5 to 25% by weight and (e) finally deacetylating the optionally dried product with concentrated aqueous alkali metal hydroxide, steps (a) and (c) being carried out at a temperature of 15 to 25° C. and at a pH value of 0.3 to 0.7 and steps (b) and (e) being carried out at a temperature of 70 to 110° C. and at a pH value of 12 to 14.

It has surprisingly been found that cationic biopolymers essentially obtained by deacetylation of chitin from marine animals solve the problem stated above when the basically known process of alternate acidic and alkaline degradation is carried out in the described manner with strict adherence to the sequence of individual steps and the pH and temperature ranges. New cationic biopolymers are obtained which, despite their high molecular weight, are readily and completely soluble in organic acids and, at the same time, have superior film-forming properties. In addition, the products are light-colored, stable in storage and protected against contamination without the addition of preservatives. The substances differ so significantly in their property profile from known biopolymers that they may be regarded as new substances in their own right. Moreover, these chitosans possess antibacterial properties which further potentiate the efficacy of the acid-form active compounds, thereby further enhancing acne treatment.

The chitosans employed by the present invention are characterized as having a molecular weight ranging from about 500,000 to about 5,000,000 g/mole, preferably from about 800,000 to about 1,200,000 g/mole, and most preferably from about 900,000 to about 1,000,000; a degree of deacylation greater than 80%, preferably from about 82 to about 88%, and most preferably from about 82 to about 85%; a Brookfield viscosity of less than 5,000 mPas; and an ash content of less than 0.3% by weight, and preferably less than 0.1% by weight, based on the weight of the chitosan. It should also be noted that chitosans are not typically soluble in citric acid, which is often used as a stabilizer in acneiform compositions. Therefore, it is preferred that the acneiform compositions of the present invention be free of citric acid.

According to one embodiment of the present invention, there is provided a composition for the topical treatment of acneiform eruptions on human skin, the composition containing: (a) from about 0.01 to about 1% by weight, preferably from about 0.02 to about 0.5% by weight, and most preferably about 0.1% by weight, of chitosan, (b) from about 0.01 to about 25% by weight, preferably from about 0.1 to about 15% by weight, and most preferably from about 0.2 to about 10% by weight, of an acid-form active compound, and (c) remainder, water, all weights being based on the weight of the composition.

Due to the nature of the chitosans employed herein, i.e., high molecular weight, high degree of deacetylation, and antibacterial properties, an acne treatment composition may be formulated having either a larger amount of acid form active, due to the film-forming and solubility in organic acids properties of the chitosan, or a smaller amount of active, due to the antibacterial properties of the chitosan.

The above-disclosed composition may, if desired, contain auxiliary components such as, for example, co-active ingredients which include antibiotics, water-miscible alcohols, binders, fillers, and the like.

According to another embodiment of the present invention, there is also provided a process for treating acne involving contacting human skin with the above-disclosed composition.

What is claimed is:

1. A composition comprising:

(a) a chitosan having a molecular weight ranging from about 500,000 to about 5,000,000 g/mole and a degree of deacylation greater than 80%;

(b) an acid-based active ingredient for treating acne, and (c) water.

2. The composition of claim 1 wherein the chitosan has a molecular weight ranging from about 800,000 to about 1,200,000 and a degree of deacylation of from about 82 to about 85%.

3. The composition of claim 1 wherein the chitosan is present in the composition in an amount of from about 0.01 to about 1% by weight, based on the weight of the composition.

4. The composition of claim 1 wherein the active ingredient is selected from the group consisting of azelaic acid, benzoyl peroxide, retinoic acid, salicylic acid, and mixtures thereof.

5. The composition of claim 1 wherein the active ingredient is present in the composition in an amount of from about 0.01 to about 25% by weight, based on the weight of the composition.

6. The composition of claim 1 wherein the composition is free of citric acid.

7. A process for treating acneiform eruptions comprising contacting human skin with a composition, the composition containing:
   (a) a chitosan having a molecular weight ranging from about 500,000 to about 5,000,000 g/mole and a degree of deacylation greater than 80%;
   (b) an acid-based ingredient for treating acne, and
   (c) water.

8. The process of claim 7 wherein the chitosan has a molecular weight ranging from about 800,000 to about 1,200,000 and a degree of deacylation of from about 82 to about 85%.

9. The process of claim 7 wherein the chitosan is present in the composition in an amount of from about 0.01 to about 1% by weight, based on the weight of the composition.

10. The process of claim 7 wherein the active ingredient is selected from the group consisting of azelaic acid, benzoyl peroxide, retinoic acid, salicylic acid, and mixtures thereof.

11. The process of claim 7 wherein the active ingredient is present in an amount of from about 0.01 to about 25% by weight, based on the weight of the composition.

* * * * *